(12) United States Patent
LeCursi et al.

(10) Patent No.: US 6,781,120 B2
(45) Date of Patent: Aug. 24, 2004

(54) FABRICATION OF CHOPPER FOR PARTICLE BEAM INSTRUMENT

(75) Inventors: Nicholas LeCursi, Jackson, MI (US); Lawrence J. LeGore, Freedom, ME (US); Robert H. Jackson, III, Veazie, ME (US); C. Bronson H. Crothers, Orono, ME (US); Peter H. Kleban, Bangor, ME (US); Brian G. Frederick, Orono, ME (US)

(73) Assignees: University of Maine, Orono, ME (US); Stillwater Scientific Instruments, Orono, ME (US)

( * ) Notice: Subject to any disclaimer, the term of this patent is extended or adjusted under 35 U.S.C. 154(b) by 0 days.

(21) Appl. No.: 10/165,851

(22) Filed: Jun. 7, 2002

(65) Prior Publication Data

US 2003/0048059 A1 Mar. 13, 2003

Related U.S. Application Data

(60) Provisional application No. 60/296,850, filed on Jun. 8, 2001.

(51) Int. Cl.[7] ............................................. H01R 43/00
(52) U.S. Cl. ........................ 250/286; 250/293; 250/294; 29/825
(58) Field of Search ................................ 250/286, 293, 250/294, 296; 29/825; 313/348

(56) References Cited

U.S. PATENT DOCUMENTS 4,150,319 A * 4/1979 Nowak et al. .............. 313/348
4,437,034 A * 3/1984 Lewandowski et al. ..... 313/348
5,465,480 A * 11/1995 Karl et al. ..................... 29/825

OTHER PUBLICATIONS

Honkanen, A., et al., "Gas–silicon detector telescope for charged particle spectroscopy," *Nuclear Instrument and Methods in Physics Research A*, 395:217–225 (1997).

Vlasak, P.R., et al., "An interleaved comb ion deflection gate for m/z slection in time–of–flight mass spectrometry," *Rev. Sci. Instrum.* 67(1):68–72 (1996).

\* cited by examiner

*Primary Examiner*—Nikita Wells
*Assistant Examiner*—Anthony Quash
(74) *Attorney, Agent, or Firm*—Hamilton, Brook, Smith & Reynolds, P.C.

(57) ABSTRACT

A technique for providing a grid for a gate such as utilized in gating a stream of ions or other particles in a spectrometer instrument. The grid of wires may, for example, be a so-called Bradbury-Nielson Gate that consists of a set of two electrically isolated sets of equally spaced wires that lie substantially in the same plane and alternate in potential. The method utilized to provide is to first fabricate a frame of an insulating substrate having a hole and depositing metal film patterns such that conductive portions are formed on either side of the hole. Conductive portions on either side form a series of terminating pads on the portion of the substrate closest to the hole and a bus bar. Grid wires are then formed by stretching a section of wire with desired constant tension across the hole and bonding the ends of the wire to a respective one of the pads on one side and bus bar on the other side. The method provides a rapid, inexpensive way to fabricate such modulating devices.

15 Claims, 6 Drawing Sheets

FABRICATION OF CHOPPER FOR PARTICLE BEAM INSTRUMENT

CROSS REFERENCE TO RELATED APPLICATION

This application claims the benefit of a prior U.S. Provisional Patent Application Ser. No. 60/296,850 filed Jun. 8, 2001 entitled "Method For Enhancement Of Electron Spectrometer Operation Using Maximum Likelihood Spectral Estimation Techniques," the entire teachings of which are hereby incorporated by reference.

BACKGROUND OF THE INVENTION

The present invention relates generally to a method for manufacturing a grid for gating a stream of charged particles.

Certain types of particle measurement instruments, such as ion mobility spectrometers, can require a gating device for turning on and off of a flowing stream of ions or other charged particles. This is accomplished by disposing a wire grid within the path of the ions; alternately energizing or de-energizing the grid then respectively traps the ions or allows them to flow.

Certain types of time of flight spectrometers, such as those described in the paper by Vlasak, P. R., et al., entitled "An interleaved comb ion deflection gate for m/z selection in time-of-flight mass spectrometery," in *Review of Scientific Instruments*, Vol. 67, No. 1, January 1996, pp. 68–72, also utilize a gating device.

The most common methods for accomplishing this use an interleaved comb of wires also referred to as a Bradbury-Nielson Gate. Such a gate consists of two electrically isolated sets of equally spaced wires that lie in the same plane and alternate in potential. When a zero potential is applied to the wires relative to the energy of the charged particles, the trajectory of the charged particle beam is not deflected by the gate. To deflect the beam, bias potentials of equal magnitude and opposite polarity are applied to the two sets of wires. This deflection produces two separate beams, each of whose intensity maximum makes an angle alpha with respect to the path of the un-deflected beam.

One approach to manufacturing a gating grid is disclosed in U.S. Pat. No. 4,150,319 issued to Nowak, et al. In this technique, a ring-shaped frame is fabricated from a ceramic or other suitable high temperature material. The two sets of wires are wound or laced on the frame. Each set of wires is actually a single, continuous wire strand that is laced back and forth between two concentric series of through-holes that are accurately drilled around the periphery of the frame.

Another technique for manufacturing such a gate is described in U.S. Pat. No. 5,465,480 issued to Karl, et al. In this approach, the gating grid elements are produced from a thin metal foil by cutting or etching the foil to produce the grid structure. The gird elements are connected to side electrodes in a desired pattern to produce the two sets of wires. The foil grid structure is made mechanically stable by attaching it to an insulating support member. After the then-rigid grid structure is affixed to the insulating support member, the grid elements are selectively severed from the side electrodes to form the interdigitated grid.

Yet another approach for manufacturing such a grid is described in the paper by Kimmel, J. R., et al., entitled "Novel Method for the Production of Finely Spaced Bradbury-Nielson Gates," in *Review of Scientific Instruments*, Vol. 72, No. 12, December 2001, pp. 4354–4357. In this method, a guide is first manufactured out of a polymer block. The guide has a series of evenly spaced parallel grooves. A hole is drilled through the center of the polymer block; this hole eventually carries the ion beam. The machined polymer block is mounted on an insulated face of an H-shaped portion of a single sided, copper clad circuit board, with the grooves running from top to bottom of the H. The polymer-to-copper clad contacts are then fixed using an epoxy. Two small portions of the single sided copper clad board are fixed on the bottom side of the polymer in the region where the block extends over the center bar of the H-shaped copper frame.

A hand cranked, rotating screw is then used as a weaving instrument. In particular, a gold-plated tungsten wire runs from a spool over a directing screw and is coupled to the hand cranked screw by a belt. The loose end of the wire is then fixed such as by using an epoxy. A weight is hung from the wire between the directing screw and the spool in order to provide a constant tension on the wire.

Beginning at one side of the center hole, the hand crank is turned, which rotates the frame, drawing the thread from the spool. While watching through a microscope, an assembler feeds a first wire set through alternating grooves in the surface of the polymer and around the frame, making sure to touch both contacts on each pass. After winding the wire across the entire width of the opening, the wire is bound to both copper contacts on either side of the hole using an epoxy. A razor blade is then used to remove the segment of the wire between the two contacts on the side of the frame opposite the polymer.

Using the same procedure as for the first wire set, a second wire set is then wound through the grooves located between the wires of the first set. The ends of the wires are then cut, leaving wire only on the polymer side of the frame.

SUMMARY OF THE INVENTION

There are deficiencies with each of the prior art approaches to fabricating such grid elements. For example, the technique described in the Nowak patent relies upon the precise placement of two sets of aligned holes on either side of a ring. Since it uses a single strand of wire which is hand woven through the holes, it does not take into consideration the need to assure a constant mechanical tension among wires in the assembled grid. Unless the mechanical tension is relatively uniform across all wires of the grid, undesirable artifacts are introduced by irregular tension. For example, at elevated operating temperatures, the larger coefficient of expansion of the metal as compared to the ceramic support could also cause the wires to sag, potentially shorting them out if they are not properly pre-tensioned. Likewise, the imprecise nature of tensioning the wire by hand often leads to wires that are not uniformly parallel. Therefore, the field normal to the grid does not decay as rapidly as theoretically possible.

Additionally, for high speed applications, the phase delays resulting from propagation of the bias current along the single continuous strands from the contact point may cause the ions to experience a deflection at different times, depending upon where they happen to be in the beam path.

Furthermore, because the frame in Nowak is circular, the individual wires are of different lengths. This means that each wire then presents a different characteristic impedance to current flowing through it. This likewise introduces different effects to different ions, depending upon where they happen to be in the beam path. Thus, ions traveling the center of the beam are subjected to a different electrical force than ions traveling in the outer portion of the beam where the grid wires are shorter.

Finally, the required thickness of the support structure in Nowak limits how closely two grids can be placed with respect to each other.

Kimmel's approach, similar to Nowak's, weaves a single thread around a frame. It also requires the assembler to carefully feed the wire through one of the alternately spaced grooves. The individual wires in the set are then bound to the copper contacts using epoxy. The method of machining a polymer block to small tolerances of 0.005 mm for each grid wire can require relatively expensive machine tools.

Furthermore, if the single wire breaks during winding or any part of the process one must start over again, from the beginning, to restring the wire. The assembly procedure envisioned is apparently so tedious that Kimmel himself estimates that it takes approximately three hours to manufacture a single gate.

The presence of large amounts of insulating polymer surfaces near the beam path may cause substantial charging effects which could be detrimental to the operation of the gate, particularly for gating low energy electrons. Furthermore, a device formed from a polymer with epoxy bindings may not survive the high expected operating temperatures of some applications such as ion mobility spectroscopy.

The process described in the Karl patent does provide a grid having wires with uniform tension. A separate support structure for the foil-like grid element is be fabricated from tubes and the thin metal foil must then be attached to the grid structure. This geometry is apparently convenient for ion mobility spectroscopy, but does not allow slit or apertures to be spaced closely on both sides. While the rapid charging and discharging of the gate is facilitated by the bus-like structure, the "ears" extending beyond the gate are likely to produce strong reflections which would be detrimental for ultra high speed operation such as in electron TOF spectroscopy. Finally, the rotational symmetry of the Karl device is not convenient for accurate alignment of the grid wires with respect to apertures placed before or after the gate.

The present invention seeks to overcome these deficiencies with a design for a gating electrode and method for fabricating it as follows.

The grid is fabricated using a substrate formed of a ceramic, such as alumina. The substrate serves as a rectangular frame for a grid of uniformly spaced wires stretched across a center rectangular hole. On either side of the frame, nearest the hole, a line of contact pads are formed.

Adjacent the line of contact pads, on the outboard side thereof, are formed a pair of bus bars. The contact pads and bus bars provide a way to connect the wires into the desired two separate wire sets of alternating potential. Specifically, the pads formed on each side of the opening serve as contact points for one end of each wire. The pads are alternately and evenly spaced along each side of the opening, inboard of the bus bars. In a preferred embodiment, the pads may be spaced, for example, down each side of the center opening. The pads serve as electrically open termination points for the ends of the grid wires that are not connected to the bus bars.

The bus bars serve to interconnect wires that belong to a given wire set.

Steps are also performed for fabrication of the grid according to the invention. First, the support frame is made from an insulating substrate such as alumina. A rectangular shaped center hole is formed in the alumina or other ceramic. The support frame, which may be laser cut, for example, may be one inch by one inch with a one-half inch by one-half inch hole placed in its center.

Metal film is then deposited on the surface of both sides of the ceramic through vacuum evaporation of gold, using chrome as an adhesion layer, for example. The metal film is then patterned on the front side to form the conducting elements on either side of the hole. These conducting elements include the ground plane, left and right bus bars, and pad elements. The desired metalization pattern can be defined by a photo-resist and chemical-etch process, a lift-off process, or by using a physical mask during an evaporation. The metal on the back side remains, as deposited, to serve as a ground plane.

In the next sequence of steps, the grid wires are attached to the fabricated frame. In this process, a spool of wire is provided that will serve as grid wires. In one preferred embodiment, the wire is a 0.002-inch diameter gold wire and the spacing of adjacent wires is 0.020-inch, to achieve a transmission of approximately 90%. A tensioner is provided to place constant tension on the wire. The spool, for example, may be arranged on a mandrel, and a hanging weight attached to the end of a string wrapped around the mandrel. The weight is adjusted to tension the wire at a specific chosen value less than the yield strength of the wire.

The free end of the wire is then fixed to a wire clamp so that it may be precisely located with respect to the tip of a parallel gap welder. The frame is then moved so that the first pad on the left hand side of the frame is located under the tip. At this point, the wire is bonded to the center of the pad. The parallel gap welder provides a relatively immediate bond of the wire to the pad. The assembler can then pull the free end of the wire to break it free from the bond, or wait until later to cut off the free ends of all of the wires.

The wire is then bonded to the bus bar on the right hand side of the frame. The free end of the wire is then pulled to break it free from this bond pad, or it is cut.

In a next step, the frame is moved so that the bus bar on the left is located under the tip and the wire is centered between the first and second pad. The wire is then bonded to the left bus bar.

The free end of the wire is then pulled to break it free from the bond and the wire is then bonded to the center of the next available pad on the right hand side of the frame. The free end of the wire is then pulled to break the wire free from the bond, or the wire is cut at this point.

The process is then repeated to produce a parallel grid of uniformly spaced and tensioned wires at a uniform distance apart from each other. By individually fixing the free end of the wire, such as by parallel gap welding it to either the pad or the bus bar on one side of the frame while keeping the wire at a constant tension and then bonding it to the opposite side of the frame, absolute consistency in the tension applied to each wire of the entire grid is assured.

This wiring process can proceed by hand, by using a mechanical stage to accurately and easily position the assembly with respect to the tip of the welder. It can also be a computer controlled process similar to that used in the wire bonding of semiconductor devices into packages.

Fabricating the bus bar and termination pads as a patterned metal film on a ceramic substrate also produces an advantage that prior art techniques do not. In particular, the bus bars and wires form a characteristic impedance that is presented to the electronic circuitry that drives the grid voltage. By keeping the bus bars at a controlled tolerance in terms of their thickness and width on the ceramic substrate, as well as the size of the pads, the characteristic impedance of the wire grid assembly and, in particular, the bus bar itself, can be assured to match that of the driver circuitry. This, in turn, further eliminates another inconsistency with prior art approaches.

The method also allows fabrication of gates with wires several times smaller in diameter than that utilized by other methods.

The square shape of the center hole allows precise alignment of the orientation of the grid wires.

The metalized surfaces of the ceramic reduce the possibility of surface charge build-up during operation, since both the "front" as well as the "back" are metalized.

The wire can be selected to decrease the thermal coefficient of expansion of the wire relative to the ceramic, for example, using Alloy 46.

A grid constructed according to the invention also lends itself to implementation in quadrupole and higher order multipole structures. For example, two grids may be placed face to face—in this case the spacing between the grids needs to be similar to the spacing between the wires. Nowak and similar prior art approaches that use relatively thick frames do not lend themselves to implementation in such multipole structures.

For example, the bus bars and the wires can be placed symmetrically with respect to a centerline of the support frame, such that by placing a second grid over the first, the bars of the same polarity are opposing each other (to avoid arcing between +V and −V) while wires of opposite polarity were opposing each other so as to produce a quadrupole field. The quadrupole field has a higher deflecting power for the same applied voltage, which reduces energy corruption effects.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention can be used to manufacture an interleaved comb of wires known as a Bradbury-Nielson Gate. Such a gate consists of two electrically isolated sets of equally spaced wires that lie in the same plane and alternate in applied voltage potential.

These gates are generally recognized as having a much smaller effective field size than the more commonly used deflection plates. They can, for example, be used to modulate ion beams in time-of-flight mass spectrometers (TOF-MS), to achieve mass-to-charge selection. Such gates are also commonly used in ion mobility mass spectrometers to regulate the injection of ion packets into a drift tube.

They have also been applied to Hadmard time-of-flight mass spectrometers to modulate the source of ion beam with a pseudorandom sequence of on and off pulses. Because the detected signal is then a convolution of the TOF mass spectra, the signal can be deconvoluted by again applying the pseudorandom sequence to yield the single mass spectrum. The resulting resolution of the instrument depends on the modulation switching time, that is, how fast the necessary voltage can be applied to the wires.

Figure 1:
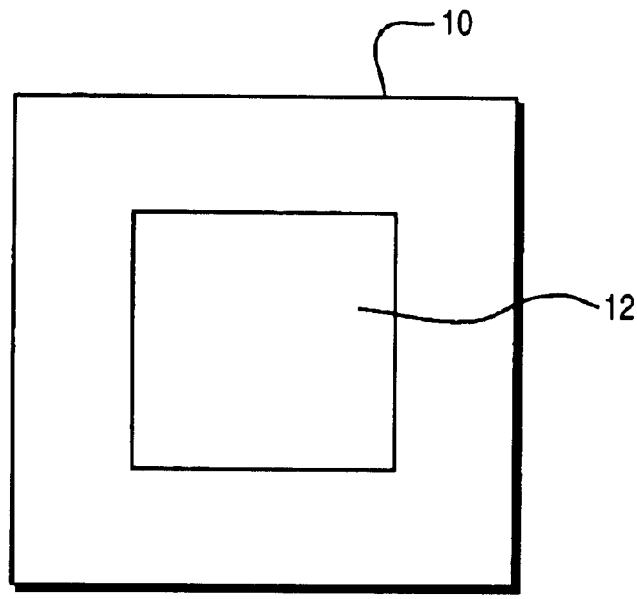
FIG. 1 is a plan view of the results of a first step of fabricating the frame in which the center hole has been cut.

FIG. 1 is an illustration of a frame 10 utilized for providing a substrate for a wire grid manufactured according to the present invention. The frame 10 consists of an insulating rigid material, typically a ceramic such as alumina. The frame 10 may have an exterior dimension of, for example, one inch by one inch, with a thickness of 0.015 inch. A hole 12 is cut in the center of the substrate material; here, the hole is approximately 0.5 inch by 0.5 inch. The hole may be cut by using a laser.

Figure 2:
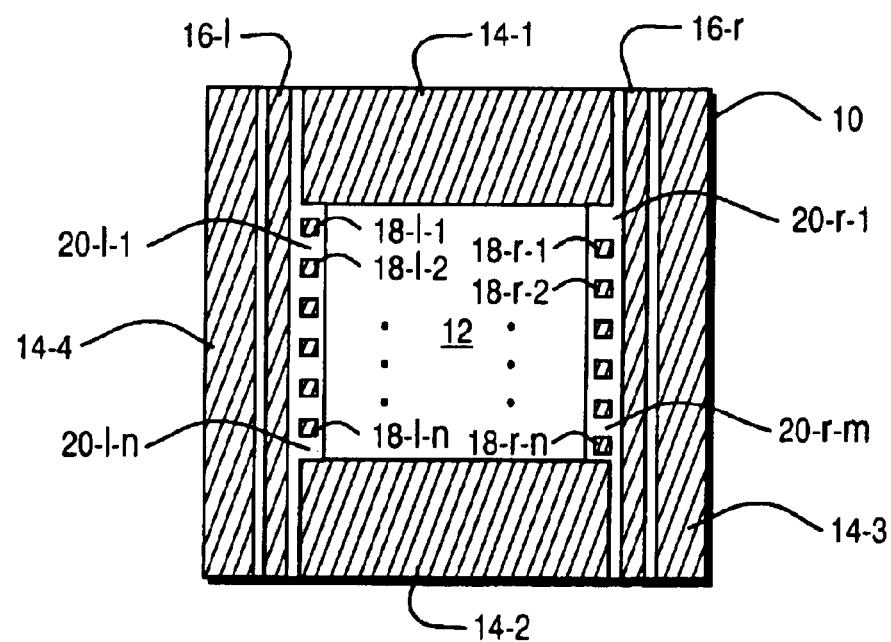
FIG. 2 is a view of the frame after a second step showing metalization patterns for ground plane bus bar and pads.

The next step is to deposit a metal film of a desired pattern. One such pattern is shown in FIG. 2. The pattern includes, for example, ground plane area 14-1, 14-2, 14-3, 14-4 (collectively, the ground plane areas 14), bus bars 16-L, 16-R, and pads 18-L-1, 18-L-2, . . . 18-L-n, and 18-R-1, 18-R-2, . . . 18-R-m.

The metalization pattern can be manufactured by depositing a metal film on the surface of the ceramic substrate. Numerous techniques are known for accomplishing this. In a preferred embodiment, this can be by vacuum evaporation of gold with a chrome adhesion layer. The metalization patterns can then be defined, for example, by a photo resist and chemical etch process.

The ground plane areas 14 generally surround the periphery of the frame 10. They serve to electrically define the region surrounding the grid of wires that are eventually strung across the hole 12.

As will be understood shortly, the bus bars 16 provide a way to electrically connect each of the two sets of grid wires. Bus bar 16-L, located on the left side of the frame, will be used to interconnect wires that terminate on the right side of the frame. Likewise, bus bar 16-R, located on the right side of the frame, is used to interconnect wires that terminate on the left side of the frame.

The pads 18 provide a place to terminate one end of the respective wires. A first set of pads 18-L-1, 18-L-2, . . . 18-L-n run along the left side of the frame adjacent the center hole 12. A second set of pads 18-R-1, 18-R-2, . . . 18-R-n run along the right side of the frame, also adjacent the hole 12. Note that the pads 18 are defined such that metal is etched around the periphery on all four sides thereof. This isolates the pad 18-L-1 from the pad 18-L-2, for example, providing an electrically open termination point.

The spacing of the pads 18 in a vertical direction is chosen to be approximately twice the desired ultimate spacing of the wires. For example, if it is desired to produce a parallel grid of two sets of uniformly spaced and tensioned wires at a grid spacing of 0.020 inches apart, the spacing between the pads 18-L on the left side of the frame should be 0.040 inches. A similar set of pads 18-R run along the right hand side of the hole 12 and serve to terminate the second set of wires; whereas the first set of pads 18-L terminate the first set of wires.

Please note that the pads 18-L on the left side of the frame are offset in vertical orientation with respect to the pads 18-R on the right side of the frame. This offset is equal to the desired spacing between the grid wires; that is, 0.020 inches in the preferred embodiment. This provides a series of spaces 20-L-1 . . . 20-L-n on the left side of the frame, and, similarly, 20-R-1 . . . 20-R-m on the right hand side of the frame. As will be understood shortly, these spaces are important in that they provide a way for the wire to pass by a pad and connect to a bus bar without shorting to an adjacent one of the pads 18 on the side opposite in which it originated.

After fabricating the metalization pattern on the frame 10, a next sequence of steps is used to attach grid wires across the hole 12. Specifically, each grid wire is stretched from one side of the frame across to the other. One end of each grid wire ends up being attached to a section of a bus bar 16; the other end of each grid wire is attached to one of the pads 18.

Figure 3:
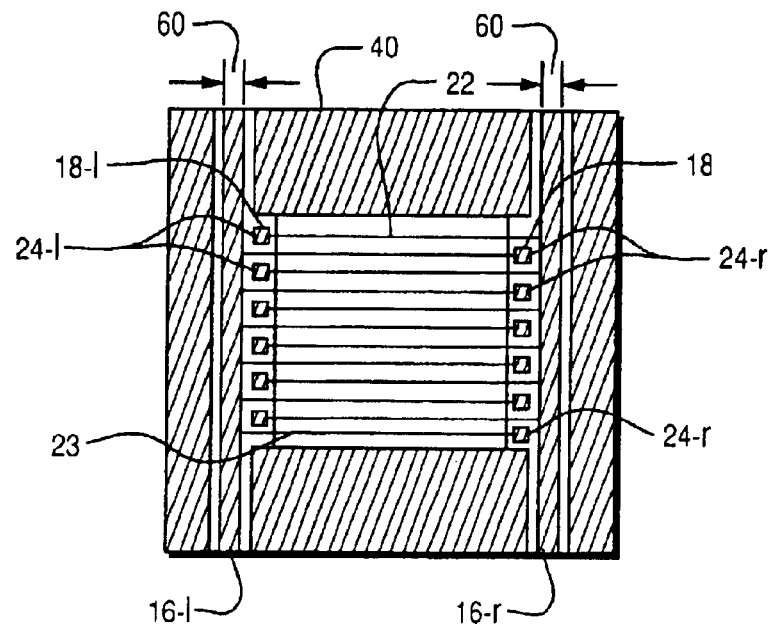
FIG. 3 is a plan view of the complete grid.

Turning more specifically now to FIG. 3, there is shown a drawing of the completed grid. Note that the grid wires 22 have been strung across the hole. Each wire connects to a bus bar on one end and a pad on the other end. Specifically, the first set of the grid wires 24-1 have one end which is connected to a respective one of the termination pads 18-L on the left side of the frame. Each of the wires in this first set 24-1 then connects to the common bus bar 16-2 on the right hand side of the frame. A second set of the grid wires 24-2 have a first end that connect to the common bus bar 16-L and terminate at one of the termination pads 18-R located on the right side of the frame.

Figure 4:
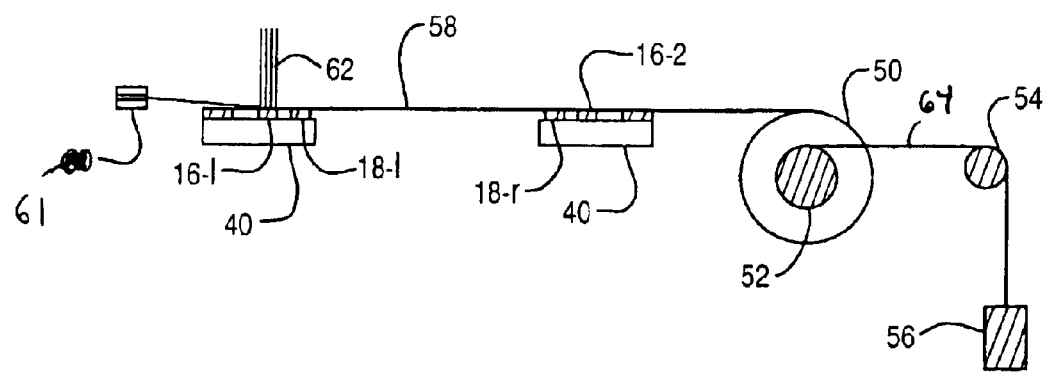
FIG. 4 illustrates a portion of process for maintaining constant tension on the wire.

A diagram illustrating a configuration for attaching the wires in this desired form is shown in FIG. 4. Provided are a wire spool 50 and tensioner, including mandrel 52, pulley 54, string 64, and weight 56. A welding tip 62 such as from a parallel gap welder is also provided.

The wire 58, in a preferred embodiment, is a gold wire of a diameter of 0.002 inches.

The tensioner is provided by mounting a spool on the mandrel 52. A respective first end of the string 64 is wrapped around the mandrel 52 and is then fed across one or more pulleys 54 to a weight 56. The weight 56 is allowed to hang freely. The amount of the weight is chosen to adjust the tension on a section of the wire 58 that is then stretched across the top portion of the frame 40.

A x-y positioning stage 68 is provided which can precisely locate the frame in two orthogonal directions.

An assembly process can now be described with reference to FIG. 4, which is a side view of one initial step, while also referring to FIGS. 5–8, which are views taken from above during assembly. A center line 70 reference in FIGS. 5–8 illustrate how the frame can be positioned by an x-y positioning stage 68—that is movable with respect to the welding tip 62, to permit attachment of the wires to the bus bars 16 and pads 18.

In a first assembly step, the free end of the wire is taken from the spool 50 and lead through a guide 72, terminating in a wire clamp 61. The wire clamp 61 provides a way to locate the wire 58 with respect to the tip 62.

Figure 5:
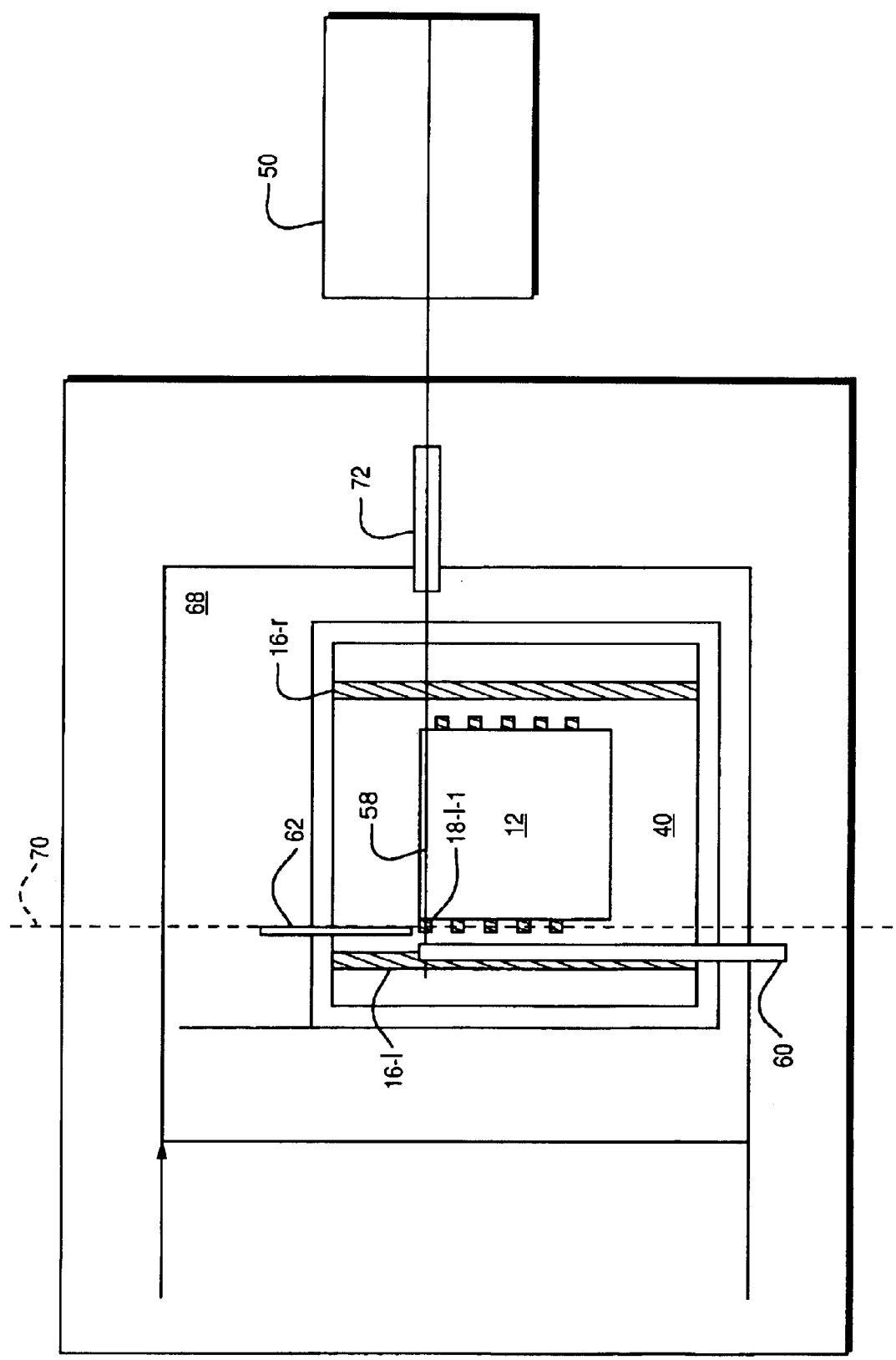
FIGS. 5–8 show how the frame is moved with respect to the bonder tip during assembly.

In a next step to produce a grid, the frame 40 is moved so that the tip 62 is centered on the first pad 18-L-1 on the left side of the frame, as shown in FIG. 5. Welding tip 62 is then placed in close contact with the pad 18-L-1 to bond the wire to the center of pad 18-L-1. A portion of the wire to the left of the pad is then pulled or bent to break it free from the bond. However, it should be understood that these free ends of wire, after having been released from the clamp, may be left in place and cut off later, such as with a cutting tool.

Figure 6:
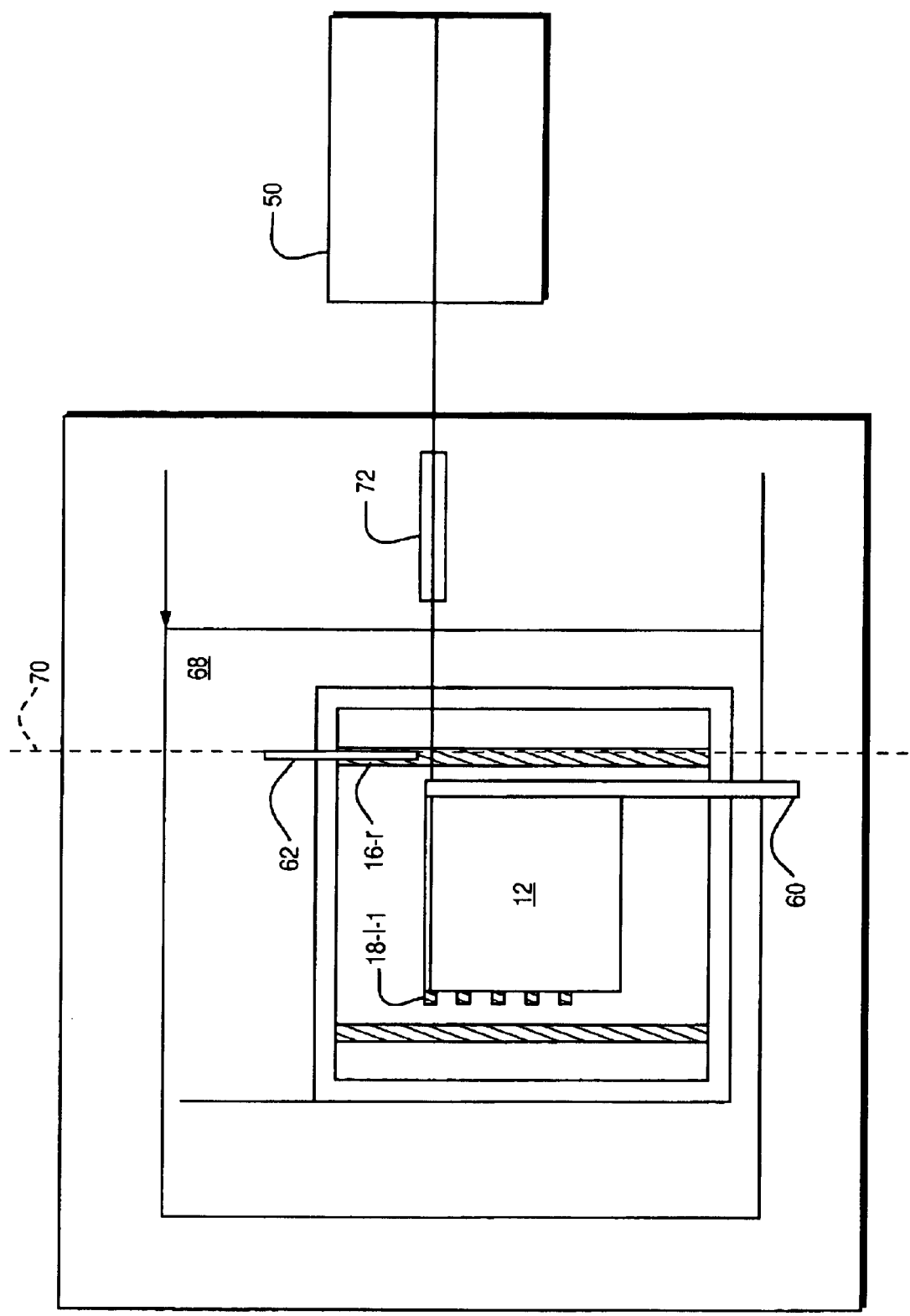

A next step is used to attach this new wire to the right side of the grid is then performed, as shown in FIG. 6. In this step, the stage 68 is moved so that the bonding tip 62 is on the right side of the frame 40. The wire, having now been attached to the pad 18-L-1 on the left side of the frame, is to be attached to the bus bar 16-R on the right side of the frame. The frame 40 is moved to the left until the tip 62 is centered on the bus bar 16-R. The frame 40 is not moved in the orthogonal direction, taking care to ensure that the wire passes through the space 20-R-1, without shorting to any adjacent pads 18-R on the right side of the frame. See FIG. 7. The wire 58 is then attached to the bus bar 16-R on the right side of the frame. This attachment is secured by parallel gap welding.

Figure 7:
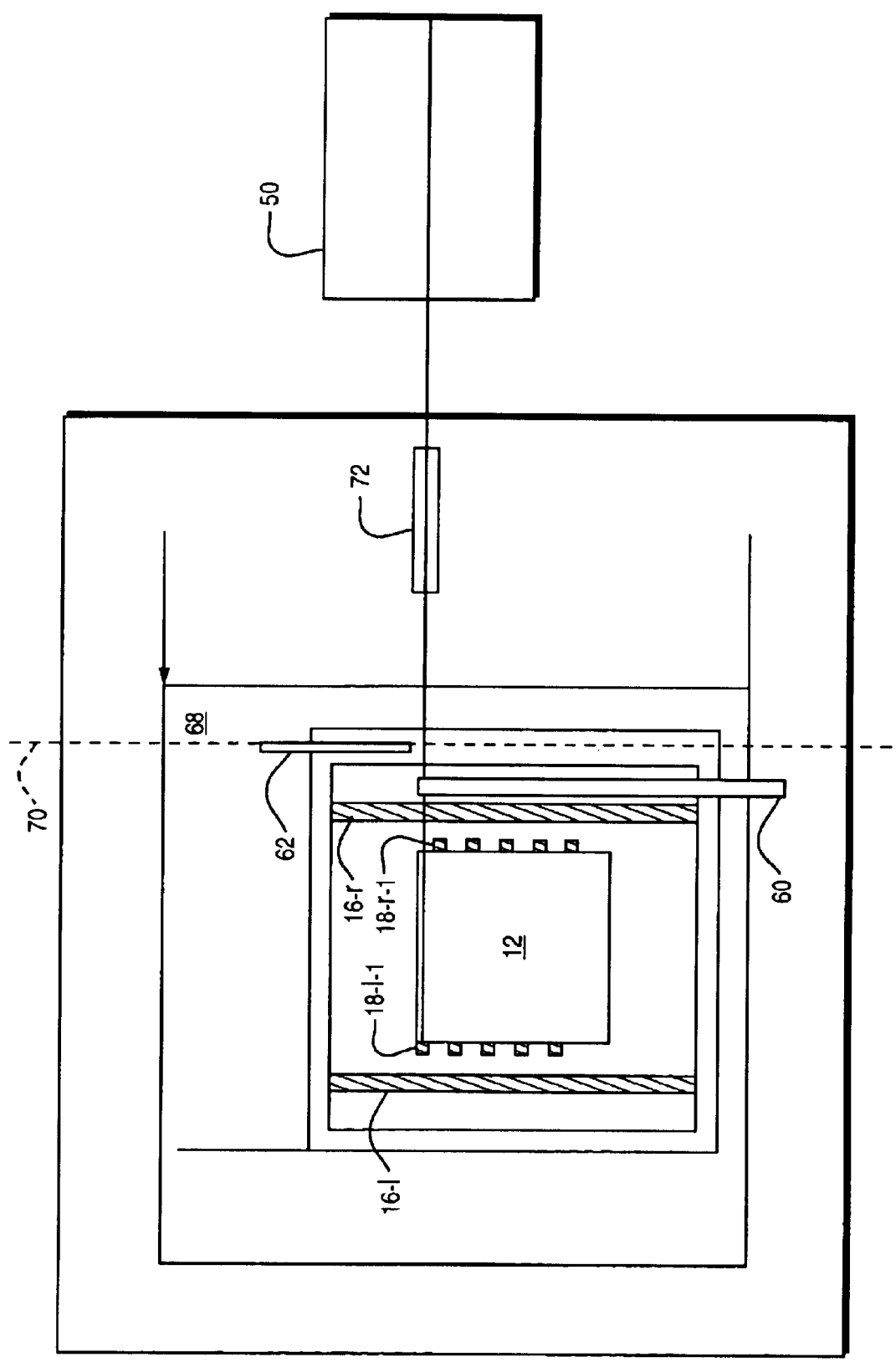

The frame 40 is then moved farther to the lefts as also shown in FIG. 7, the clamp 61 is engaged on the wire 58, and the wire 58 is then pulled to break it free from the bond, or it is cut.

Figure 8:
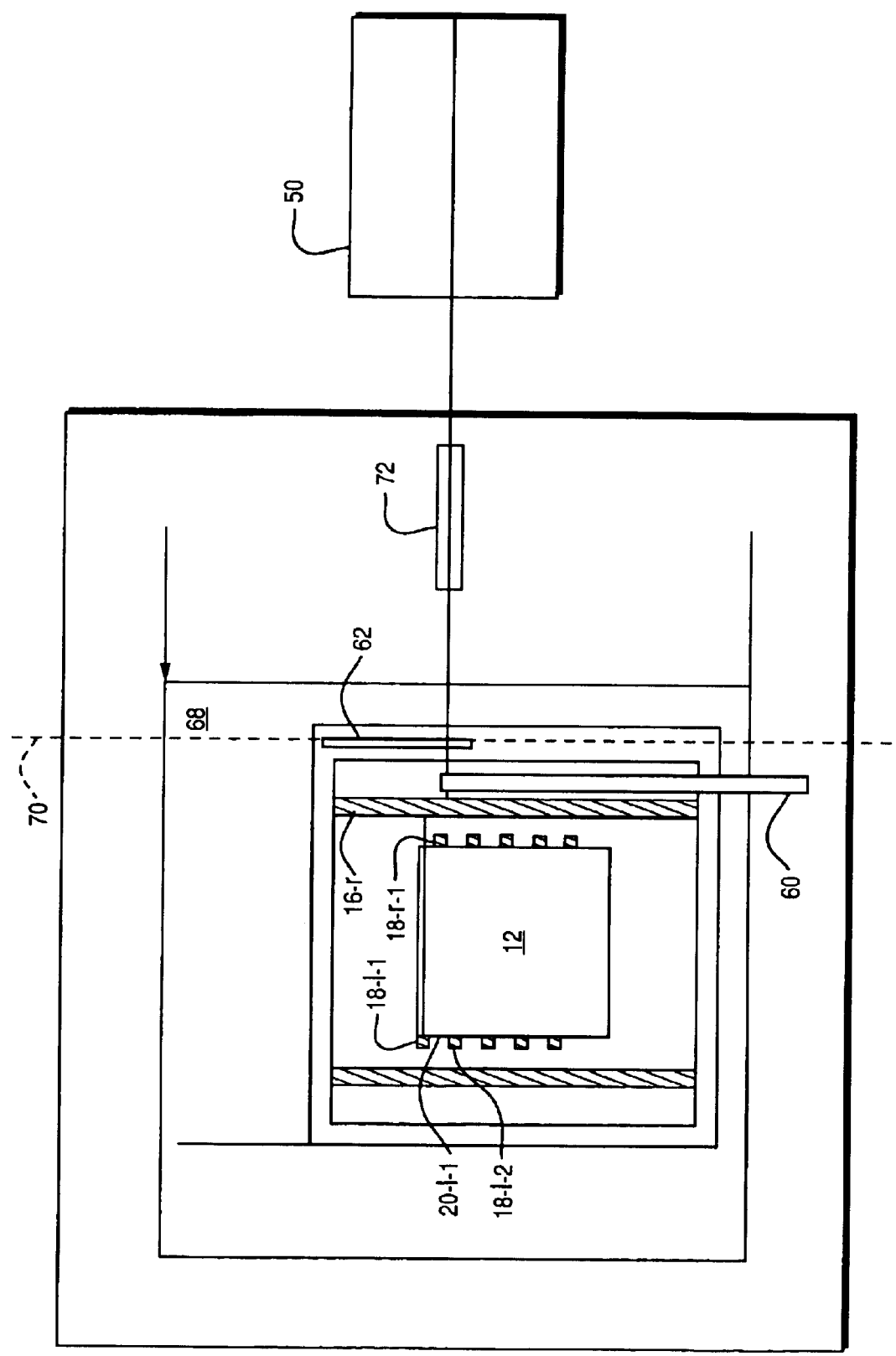

The next step is to fabricate a second wire section 23, that is a wire that terminates at a bus bar 16-L on its left side and a pad 18-R-1 on its right side. The frame is moved, as shown in FIG. 8, precisely in the orthogonal direction by, for example, a screw mechanism on the stage 68 with an attached caliber mechanism to precisely measure the location in the orthogonal direction. The frame is moved in the orthogonal direction a distance equal to the grid wire spacing which is one half the distance between adjacent pads. The frame 40 is then moved until the tip 62 is centered on the bus bar 16-L on the left, similar to FIG. 5. Again, the frame 40 is not moved in the orthogonal direction ensuring that the wire passes through the space 20-L-1 between the first pad 18-L-1 and second pad 18-L-2 on the left side of the frame so that it does not short to either of those pads. The wire is then bonded to the bus bar 16-L on the left side of the frame. The free end of the wire is then pulled to break it free from the bond, or left to be cut off later on.

The frame 40 is then moved until the tip 62 is centered on the pad 18-R-1 on the right side of the frame. After being bonded with the parallel gap welder, it is cut from the bond or otherwise broken.

This procedure is then repeated a number of times, to produce a parallel grid of two sets of wires that are uniformly spaced and tensioned.

It can be seen now how the bus bars 16-L and 16-R provide a convenient way to interconnect the wires associated with the respective one of the two sets. The inventors have also recognized that the bus bars 16 should be carefully chosen in their specific width 60 and film depth. Specifically, the bus bars 16 represent (as any electrical circuit) an impedance to the circuitry that drives the respective wire grid with the modulation voltage. The width of gold wires represent an electrical impedance and thus act in a way that is quite similar to a microstrip transmission line. A respective characteristic impedance of the bus bar and wire grid structure can thus be determined to optimize transmission of the electrical signal from the modulation circuitry to the grid. The width of the bus bars 16 is then chosen to match the characteristic impedance. In a preferred embodiment with a characteristic design characteristic impedance of 50 ohms and dimensions of the wire grid stated above, the width of the bus bar 16 is approximately 0.017 inches when the bus bar length is approximately 1 inch. The metalization pattern may be controlled such that the depth is about 0.010 mm.

It would also be convenient to pattern the gold such that surface mount resistors can be placed between the bus bars and the ground plane region, so as to provide on-board termination of the transmission line signals, especially for low voltage applications where total power dissipation is not a problem.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for manufacturing a gating grid for a charged particle stream, the gating grid comprising a first and second set of electrically isolated, equally spaced wires that lie in the same plane, the respective sets of wires to be applied to alternate potentials, the method comprising the steps of:

selecting an insulating substrate material to serve as a frame for a gating grid;

patterning a set of conductive portions on opposing sides of a hole formed in the substrate;

aligning a first individual section of wire from a conductive portion on one side of the hole, across the hole to a conductive portion on a second side of the hole;

tensioning the individual wire section thus stretched from one side of the hole to the other side; and bonding first one side of the individual wire section to the conductive portion on one side of the hole and then next bonding the same individual wire section to the second conductive portion on the other side of the hole; and repeating the steps of aligning, tensioning, and bonding other individual sections of wire.

2. A method according to claim 1 wherein the individual wire sections are attached to the patterned conductive portions using a parallel gap welder.

3. A method as in claim 1 wherein the substrate is formed from alumina.

4. A grid as in claim 1 wherein the impedance of the bus bars matches that of a driving electronic component.

5. A grid as in claim 1 wherein the bus bars are arranged for termination by a terminating resistor.

6. A method as in claim 1 wherein the conductive portions are formed as a bus bar and isolating pads respectively.

7. A method as in claim 6 wherein along each side of the frame, a bus bar is formed outboard of a series of isolating pads, with the isolating pads formed on the inboard portion of the substrate closest to the hole.

8. A method as in claim 6 wherein the isolating pads are spaced at a distance which is twice the desired spacing of the grid wires.

9. A method as in claim 6 wherein the width of the bus bars formed in the patterning step is chosen to match the bus bar impedance to a desired characteristic impedance of driving circuitry.

10. A method as in claim 6 wherein the grid is used for an electron particle stream in a time of flight (TOF) spectrometer.

11. A method as in claim 1 wherein the conductive portions are patterned on the substrate by the steps of:

depositing a metal; and defining a pattern by a process selected from a group consisting of a chemical etch process, a lift-off process, and a physical mask during the metal deposition step.

12. A method as in claim 11 wherein the step of depositing a metal film is carried out through application of an adhesion layer followed by deposition of the metal.

13. A method of fabricating a gating grid for use in a particle beam measurement device, the gating grid having a first and second set of parallel spaced wires for providing an electric potential to the grid, the method comprising the steps of:

providing an insulating substrate;

cutting a hole in a center portion of the insulating substrate;

patterning a conductive layer on the top portion of the substrate, the conductive layer providing on each side of the hole a first series of conductive pads spaced at twice the distance of the resulting desired grid wire spacing, the conductive pads located on the inboard side of the frame closest to the hole and also defining a bus bar running in parallel with the conductive pads positioned outboard of the conductive pads;

providing a wire grid portion with controlled tension via the steps of:
  (a) aligning a wire across the substrate from a first side of the hole to a second side of the hole;
  (b) bonding the wire to a center portion of a first one of the pads at one side of the hole;
  (c) bonding the wire to a bus bar on the opposite side of the frame;
  (d) breaking the end of the wire;
  (e) stretching the wire from a second pad on the second side of the hole across the hole to the bus bar on the first side of the hole;
  (f) bonding the wire to each of the respective pad and bus bar;
  (g) breaking the end of the wire; and repeating steps (a) through (a) to provide additional wires for the wire grid.

14. A method as in claim 13 wherein the width of the bus bar is formed such that it matches a desired characteristic impedance of circuitry used to drive voltages to the grid.

15. A method as in claim 13 wherein the wire is held under tension during the bonding steps (c) and (f).

* * * * *

UNITED STATES PATENT AND TRADEMARK OFFICE
CERTIFICATE OF CORRECTION

PATENT NO. : 6,781,120 B2
DATED : August 24, 2004
INVENTOR(S) : Nicholas LeCursi et al.

It is certified that error appears in the above-identified patent and that said Letters Patent is hereby corrected as shown below:

Column 10,
Line 46, delete "(a) to provide" and insert -- (g) to provide --

Signed and Sealed this

Fourteenth Day of December, 2004

JON W. DUDAS
*Director of the United States Patent and Trademark Office*